(12) United States Patent
Mayor Sans et al.

(10) Patent No.: US 9,925,290 B2
(45) Date of Patent: Mar. 27, 2018

(54) SYSTEM FOR DELIVERING VOLATILE SUBSTANCES

(71) Applicant: Zobele Espana, S.A., Barcelona (ES)

(72) Inventors: Fernando Mayor Sans, Barcelona (ES); Elisabeth Martinez de Morentin Pujabet, Barcelona (ES); Joaquim Llorente Alonso, Barcelona (ES)

(73) Assignee: Zobele Espana, S.A., Barcelona (ES)

( * ) Notice: Subject to any disclaimer, the term of this patent is extended or adjusted under 35 U.S.C. 154(b) by 6 days.

(21) Appl. No.: 14/071,176

(22) Filed: Nov. 4, 2013

(65) Prior Publication Data

US 2014/0124593 A1     May 8, 2014

(30) Foreign Application Priority Data

Nov. 6, 2012  (EP) ..................................... 12382429

(51) Int. Cl.
    *A61L 9/12*    (2006.01)
(52) U.S. Cl.
    CPC .............. *A61L 9/12* (2013.01); *A61L 2209/11* (2013.01)
(58) Field of Classification Search
    CPC ........................................................ A61L 9/12
    USPC ...................... 239/34–60; 222/547, 548, 565
    See application file for complete search history.

(56) References Cited

U.S. PATENT DOCUMENTS

| 2,765,194 | A   |   | 10/1956 | Will |
| 3,754,707 | A   | * | 8/1973  | Morane ..................... A61L 9/12 239/59 |
| 4,621,768 | A   | * | 11/1986 | Lhoste et al. ................... 239/44 |
| 5,065,889 | A   | * | 11/1991 | Conti ................... A47G 19/027 220/360 |
| 5,772,074 | A   |   | 6/1998  | Dial et al. |
| 7,243,859 | B2  | * | 7/2007  | Caserta et al. .................. 239/34 |

OTHER PUBLICATIONS

Non-Final Office action from U.S. Appl. No. 14/071,052, filed Nov. 4, 2013, 11 pgs., mailed from the United States Patent and Trademark office on Jun. 15, 2015.

* cited by examiner

*Primary Examiner* — Arthur O Hall
*Assistant Examiner* — Tuongminh Pham
(74) *Attorney, Agent, or Firm* — Baker Hostetler LLP

(57) ABSTRACT

A system for delivering volatile substances comprising a housing inside which a volatile substance is housed; a ventilation surface placed in the housing provided with ventilation windows, and a regulating element that can be placed in at least two different positions: a first position of maximum air circulation, and a second position of minimum air circulation; and where the regulating element is further characterized in that in the first position, the regulating element opens an additional ventilation opening, and in the second position, the regulating element closes the of additional ventilation opening. The system for delivering volatile substances permits easy regulation of the circulation of air for increasing or decreasing a volatile substance, for example a fragrance, by simply rotating the regulating element.

7 Claims, 2 Drawing Sheets

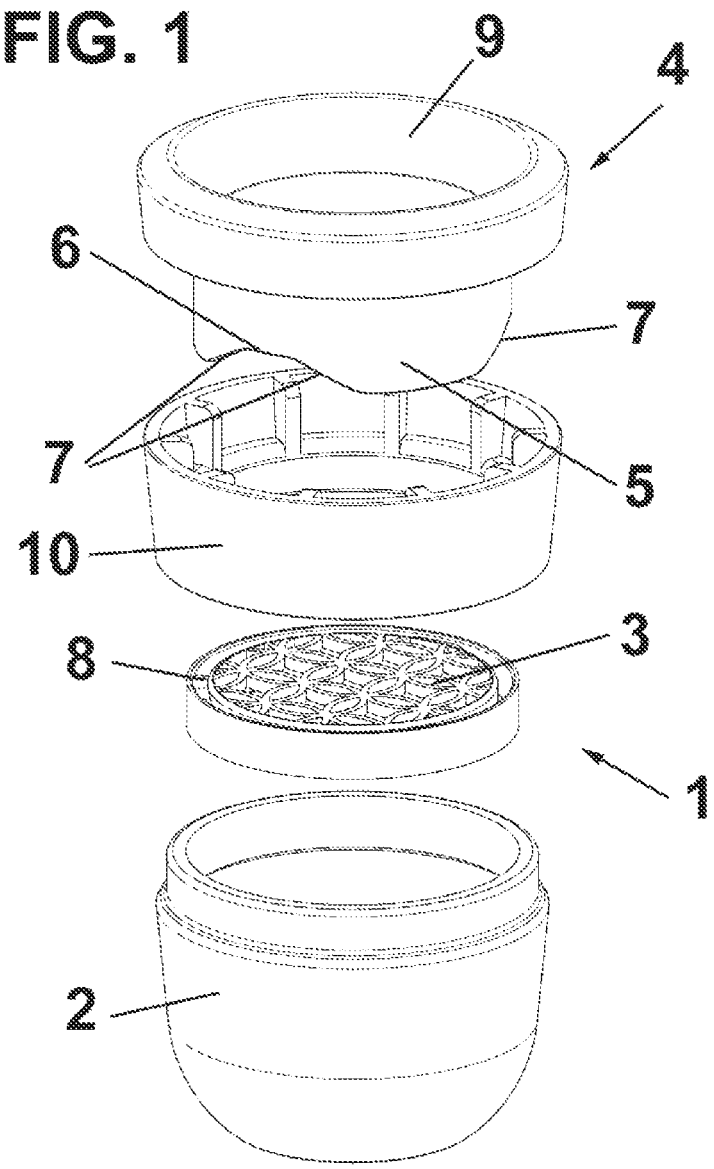

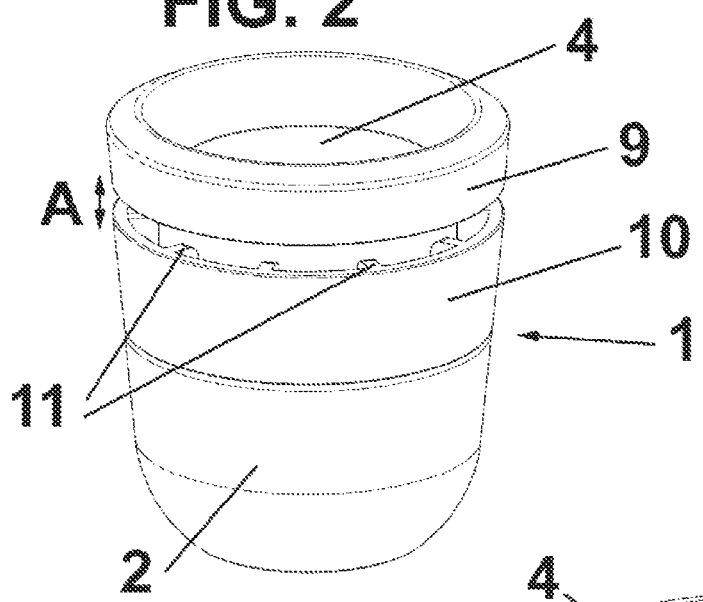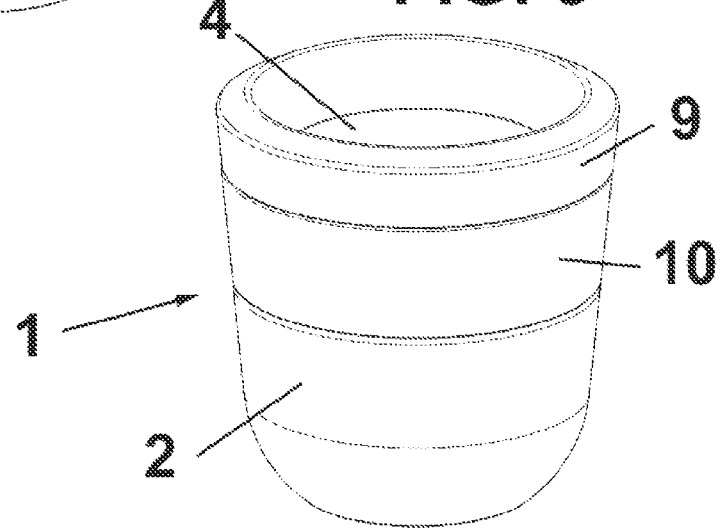

SYSTEM FOR DELIVERING VOLATILE SUBSTANCES

The present invention refers to a system for delivering volatile substances, in which the air circulation can be regulated to increase or decrease the fragrance produced by the system for delivering volatile substances. The present application claims the benefit of European Patent Application Serial No. 12382429.4, with a filing date of Nov. 6, 2012.

BACKGROUND OF THE INVENTION

A type of air fresheners or systems for delivering volatile substances currently known in the art comprises a housing or container inside of which an air freshening substance or volatile substance is housed.

During the manufacturing, said housing is hermetically sealed so that the air freshener product or volatile substance conserves its full fragrance, in such a way that when it is used the sealing or hermetic seal must be removed.

A problem with these air fresheners or systems for delivering volatile substances currently known in the art is that once this sealing or hermetic seal is opened, the system for delivering volatile substances will continue carrying out its function at the same level of intensity until the fragrance of said air freshener or volatile substance product is spent. Therefore, it is not possible to regulate the circulation of the air to increase or reduce the fragrance.

Another problem normally associated with these air fresheners or systems for delivering volatile substances is that they cannot be refilled once the fragrance of the air freshener product or volatile substance has been spent, such that in practice they are for a single use.

DESCRIPTION OF THE INVENTION

The system for delivering volatile substances of the invention enables solving the cited drawbacks and provides other advantages which are described below.

The system for delivering volatile substances of the present invention comprises:
a housing inside of which a volatile substance is housed;
a ventilation surface placed in said housing provided with ventilation windows; and
a regulating element that can be placed in at least two different positions: a first position for maximum air circulation and a second position for minimum air circulation, and it is characterized in that in said first position the regulating element opens an additional ventilation opening and, in said second position, the regulating element closes said additional ventilation opening.

Advantageously, said regulating element is rotatably mounted over said ventilation surface and, according to a preferred embodiment, comprises a skirt provided on its bottom portion with cuts with inclined sides, defining the central portion of said cuts said second closing position of said additional ventilation opening and said inclined sides positioned in intermediate positions between said first opening position of the additional ventilation opening and said second position.

Furthermore, according to said preferred embodiment, said ventilation surface comprises ribs on its perimeter that are in contact with said skirt of the regulating element, so that when said ribs are in contact with the bottom of said skirt, the regulating element is in said first opening position, when said ribs are in contact with the central portion of said cuts the regulating element is in the second closing position, and when said ribs are in contact with said inclined sides of the cuts, the regulating element is in an intermediate position.

Preferably, said regulating element comprises a ring that defines said additional ventilation opening with an intermediate element placed around said ventilation surface.

Advantageously, said ventilation surface is detachably mounted over said housing, in such a way that the housing can be filled with a volatile substance.

Preferably, said intermediate element comprises a plurality of protrusions for centering said regulating element.

With the system for delivering volatile substances of the present invention, the circulation of the air can be easily regulated to increase or reduce the fragrance, for example, simply rotating said regulating element.

Furthermore, according to the preferred embodiment, said regulating element can be placed in intermediate positions between a first opening position and a second closing position, depending on the desired regulation of the air circulation.

Advantageously, said ventilation surface is a screen that prevents access to the volatile substance in an inadvertent or undue manner, so that it is child proof.

BRIEF DESCRIPTION OF THE DRAWINGS

For a better understanding of the above explanation and for the only purpose of providing an example, some non-limiting drawings are included that schematically depict a practical embodiment.

FIG. 1 is an exploded perspective view of the system for delivering volatile substances of the present invention;

FIG. 2 is a perspective view of the system for delivering volatile substances of the present invention in its position of maximum air circulation; and FIG. 3 is a perspective view of the system for delivering volatile substances of the present invention in its position of minimum air circulation.

DESCRIPTION OF A PREFERRED EMBODIMENT

FIG. 1 depicts an exploded view of all the components of the system for delivering volatile substances of the present invention, identified generally by reference number 1.

Said system for delivering volatile substances 1 comprises a housing 2 inside of which a volatile substance or air freshener product that produces a fragrance (not shown) is housed.

A ventilation surface 3 provided with a plurality of ventilation windows is mounted on top of said housing 2 in a fixed manner that prevents direct accidental access to the freshener product or volatile substance, for example, to prevent children from touching it, while at the same time enabling said ventilation surface to be separated from the housing 2 when it is necessary to refill the housing 2 with another volatile substance, as needed. As is obvious, the air with the fragrance coming from the volatile substances passes through said ventilation surface 3 to the exterior.

The system for delivering volatile substances 1 also comprises a regulating element 4 that permits to regulate the circulation of the air, increasing or decreasing the fragrance produced by system for delivering volatile substances 1, as will be explained further on.

Said regulating element 4 is rotatably placed on top of an intermediate element 10, which in turn is placed around said ventilation surface 3. The intermediate element 10 comprises a plurality of protrusions 11 for centering said regulating element 4 with respect to said intermediate element 10.

Said intermediate element 10 defines, together with regulating element 4, an additional opening (identified as A in FIG. 2) for providing a circulation of additional air.

As can be seen in FIG. 1, said regulating element 4 comprises a skirt 5 and a ring 9. Said skirt 5 comprises some cuts 6 having inclined sides 7, whose skirt 5 permits to regulate the degree of the opening of the additional opening A.

The skirt 5 of said regulating element 4 is in contact with said ventilation surface 3, specifically, with ribs 8 located on the perimeter of said ventilation surface 3. The relative position of the regulating element 4 will determine the following regulating positions of the circulation of air.

A first position of maximum circulation of the air, depicted in FIG. 2. In this first position, the bottom part of the skirt 5 is in contact with the ribs 8 in such a way that the regulating element 4 is in its highest position, with the additional opening A being opened to its maximum extension.

A second position of minimum circulation of the air, depicted in FIG. 3. In this second position the central portion of the cuts 6 is in contact with the ribs 8, in such a way that the regulating element 4 is in its lowest position, with said additional opening A being closed.

Intermediate positions between said first and second positions, in which the inclined walls 7 of the cuts 6 are in contact with the ribs 8, with the additional opening A being partially open.

In order to be able to place the regulating element 4 in any of these positions, it is simply necessary to rotate it with respect to intermediate element 10.

Even though reference has been made to a specific embodiment of the invention, it is obvious to a person skilled in the art that the system for delivering volatile substances described herein is susceptible to numerous variations and modifications, and that all of the details mentioned can be substituted for other technically equivalent ones without departing from the scope of protection defined by the attached claims.

What is claimed is:

1. A system for delivering volatile substances comprising: a housing inside which a volatile substance is housed; a ventilation ring placed in said housing provided with ventilation windows; and a regulating element having at least two different positions: a first position of maximum air circulation wherein the regulating element is in its highest position in relation to the housing and a second position of minimum air circulation wherein the regulating element is in its lowest position in relation to the housing; wherein the regulating element is characterized in that in said first position, the regulating element opens an additional ventilation opening and in said second position, the regulating element closes said additional ventilation opening; wherein the regulating element further comprises a skirt with cuts with inclined sides provided on a bottom edge of the skirt such that when rotating said regulating element with respect to an intermediate element, a central portion of said cuts define said second closed position of said additional ventilation opening, and said inclined sides define intermediate positions between said first position of the additional ventilation opening and said second position; and wherein the ventilation ring comprises a circumferential inner surface on its perimeter, a circumferential outer surface surrounding the inner surface, and a plurality of ribs disposed between the inner surface and outer surface; wherein the plurality of ribs are in contact with the skirt of the regulating element such that when said plurality of ribs contact a bottom portion of the skirt, the regulating element is in said first position; when said plurality of ribs are in contact with the central portion of said cuts, the regulating element is in said second closed position; and when said plurality of ribs are in contact with said inclined sides of the cuts, the regulating element is in an intermediate position.

2. The system for delivering volatile substances according to claim 1, characterized in that said regulation element is rotatably mounted over said ventilation ring.

3. The system for delivering volatile substances according to claim 1, characterized in that the regulating element comprises a ring that defines said additional ventilation opening with the intermediate element placed around said ventilation ring.

4. The system for delivering volatile substances according to claim 1, characterized in that said ventilation ring is mounted in a fixed manner over said housing.

5. The system for delivering volatile substances according to claim 3, characterized in that said intermediate element comprises a plurality of protrusions for centering said regulating element.

6. The system for delivering volatile substances according to claim 1, characterized in that said ventilation ring is a screen.

7. The system for delivering volatile substances according to claim 3, characterized in that said ventilation ring is a screen.

* * * * *